United States Patent [19]

Speiser et al.

[11] 4,021,364

[45] May 3, 1977

[54] MICROCAPSULES IN THE NANOMETRIC RANGE AND A METHOD FOR THEIR PRODUCTION

[75] Inventors: Peter Speiser, Forch; Gerd Birrenbach, Aesch, both of Switzerland

[73] Assignee: Prof. Dr. Peter Speiser, Forch, Switzerland

[22] Filed: Dec. 4, 1973

[21] Appl. No.: 421,604

[30] Foreign Application Priority Data

Dec. 4, 1972 Switzerland .................. 017633/72

[52] U.S. Cl. ..................... 252/316; 252/301.1 R; 424/1; 424/33; 424/85; 424/89; 424/94; 427/5; 424/36
[51] Int. Cl.² ......................................... B01J 13/02
[58] Field of Search ............... 252/316; 424/33, 1, 424/85, 89; 117/161 UN; 260/80.3 N; 427/5, 36

[56] References Cited

UNITED STATES PATENTS

| | | | |
|---|---|---|---|
| 2,801,985 | 8/1957 | Roth ....................... | 260/80.3 N X |
| 2,969,330 | 1/1961 | Brynko ....................... | 252/316 |
| 3,427,250 | 2/1969 | Haas et al. ................. | 252/316 |
| 3,544,500 | 12/1970 | Osmond et al. ............. | 252/316 X |
| 3,577,516 | 5/1971 | Gould et al. ................ | 424/33 X |

Primary Examiner—Richard D. Lovering
Attorney, Agent, or Firm—Burns, Doane, Swecker & Mathis

[57] ABSTRACT

The present invention is concerned with novel synthetic capsules which are colloid soluble in water or suspendible or colloid soluble in hydrophobic media and consist of compatible polymeric material, more especially of acrylamide and N,N'-methylene-bis-acrylamide gel or of acrylic acid and acrylic acid methyl ester gel, which are submicroscopic and mainly micellar in size, and which contain biologically or pharmacodynamically active material, more especially proteins, antigens, pharmacologically or therapeutically active substances or pesticides, fertilizers, dyes, color forming agents, adhesives and catalysts or other technically active substances in an incorporated and/or adsorbed form, together with the method for their production and their application.

7 Claims, No Drawings

MICROCAPSULES IN THE NANOMETRIC RANGE AND A METHOD FOR THEIR PRODUCTION

BACKGROUND OF THE INVENTION

The production and application of the known microcapsules with the diameters in the range of, for example, 0.1–1 millimeters containing liquid or solid substances for medical and technical use, such as, for example, for the administration through the skin or mucous membrane, for masking the flavor of bitter drugs, encapsulations resistant to gastric juices for the protection of active substances against environmental influences, or for the encapsulation of adhesive substances which can be activated by pressure or temperature, for the manufacture of application forms of pesticides with a depot effect and for the encapsulation of dyes, are well known. The wall material of these microcapsules consists mainly of polymeric, more or less water-insoluble material such as gelatines or synthetic polymers. Microcapsulation can be performed by building up the envelope in rotating drums, plates, discs, rollers, etc., and by fluidization or spray condensation. A method commonly used at present for the production of microcapsules, is the so-called "simple" or "complex" coacervation (J. Pharm. Sc., 59, 1367 [1970]), which is a process generally comprising four stages:

a. Production of an emulsion or suspension of the enclosure substance in a suitable carrier liquid which already contains the wall material in solution,
b. Production of the wall material in the form of small droplets in this suspension or emulsion by phase separation or the addition of a further phase, a threephase system being formed in the appropriate circumstances,
c. Capsulation of the enclosure phase by the droplets of wall phase material separated in b), and
d. Solidification of the at first still liquid wall of the capsule.

Stirring must be continued during the whole process in order to maintain the stability of the multi-phase system. During this process the microcapsules are as a rule formed by coacervation of gel systems as described, for example, in Swiss Pat. Nos. 330,500 and 373,633; the German document Nos. 1,256,194 and 1,256,196 laid open to public inspection; German Pat. Nos. 1,180,347, 1,185,585 and 1,189,050; U.S. Pat. Nos. 2,800,457, 2,800,458, 3,155,590 and 3,190,837; British Pat. No. 1,016,839; Belgian Pat. Nos. 699,324, 701,600 and 727,294; and the German document No. 1,928,552 laid open for public inspection. The particle size of the microcapsules produced by these methods varies between a minimum of a few micrometers (1 micrometer = $10^{-6}$ meters) and several millimeters.

The use of such microcapsules in medicine, for example, is limited to oral, cutaneous, ipethelial and enteral administration. The purpose of the present invention is to obviate this substantial limitation imposed upon medical application and beyond that to have a form of capsule available, which has considerable advantages for many applications.

In order to ensure safe parenteral administration of therapeutically active particles, including the intravenous route, the diameter of the particles in the micrometer range, and up to several hundred micrometers, must be reduced to a few hundred nanometers ($10^{-9}$ meters). This is a 100 to 10,000-fold reduction in size of the known capsules. It is obvious that for this purpose an essentially new process must be invented and applied, resulting in particles with a diameter of less than 200 nanometers and for the most part less than 80 nanometers.

Polymer particles with a diameter between 10 micrometers and 2 millimeters are obtained by suspension polymerization according to the method described, for example, in German Pat. No. 1,081,228. The smallest particles of synthetics hitherto known have been obtained by emulsion polymerization in which the normally water-insoluble monomers are emulsified in the aqueous phase, the actual polymerization, however, occurring not in the monomeric droplets but in the aqueous phase, and in which finally an aqueous dispersion is obtained of spherical polymer particles (latex particles) with a diameter of between some 100 to several 1,000 nanometers (Fikentscher et al, Angewandte Chemie 72, pp. 856–864 [1960]; Harkins, Journal of Polymer Science, Vol. V, No. 2, pp. 217–251 [1950]).

Neither the particles obtained by suspension or emulsion polymerization are small enough to be colloid soluble in water, whereas microcapsules of micellar size can form a stable colloid solution in water.

The new method of polymerization limited to the micellar region has been developed on the basis of the existing doctrine and knowledge of emulsion polymerization, which method leads to the microcapsules according to the invention, which consist of a polymeric material, preferably of a hydrophilic gel from polymerized acrylamides, acrylic acid and/or their derivatives and which have a diameter in the nanometer range of 20–200 nanometers, preferably 80 nanometers and are colloidally soluble in water, and contains active substances in a capsulated and/or adsorbed form. The polymer preferably has a porous structure.

These micellar capsules can be produced by genuinely or at least colloidally dissolving water-soluble, polymerizable molecules and the material to be encapsulated, for example, the biologically or pharmacodynamically active substance together in water. This aqueous solution is distributed while stirring, in a hydrophobic liquid, which constitutes a phase, in which the synthetic monomers and the active substances are difficultly soluble or insoluble, with the aid of boundary surface active auxiliaries (tensides). Minute micelles, containing the polymerizable monomers, active components and possibly other auxiliary agents, are now solubilized in a relatively large volume of the hydrophobic phase and form extremely small reaction regions for the ensuing polymerization of the monomers. This is induced by the methods already known, cf., for example, German Pat. No. 1,081,228 or U.S. Pat. Nos. 2,880,152 and 1,880,153. In this process polymerization is restricted principally to the micellar regions, for the hydrophobic main phase contains no polymerizable material and even a diffusion of monomers in and through this phase is largely prevented.

To capsulate water-insoluble materials the system can be modified in such a way that a lipophilic phase with the dissolved material and oil-soluble monomers are solubilized in a hydrophilic medium, usually water. In this case the diffusion of monomers through the hydrophilic phase is largely prevented.

In contrast to emulsion polymerization, in which in most cases water-insoluble monomers polymerize in water and in which the radicalcontaining, polymerizing emulsion droplets may swell to many times their original size, due to the diffusion of monomers from the stock of the emulsion droplets present into the growing polymer-monomer particles (latex particles), "micelle polymerization" according to the present invention is limited strictly to the monomers contained in the micelles. For this reason the particles remain extremely small. By variation of monomers and wetting agents, whose concentration of the type of polymerization, and catalysts, the ratio of hydrophobic to aqueous phase and the selection of tensides as micelle generators, a controlled wetting may be procured within the micelles, a variable polymer structure, and hence a specific capsulation of the active material.

After completion of the polymerization, the solid residue is diluted with a suitable solvent, generally with an aqueous alcohol, e.g., methanol, by removal and concentration of the external phase, e.g., by distillation, ultrafiltration and centrifuging, and the polymer particles formed can usually be precipitated and extracted by the filtration of centrifuging of the soluble accompanying substances and the emulsifier.

As an alternative, after the solution has been depolymerized it can be adjusted at a suitable solvent content and the emulsion/suspension obtained can be ultrafiltered directly and the polymer isolated. In both cases the product obtained again shows colloidal behavior in suitable solvents. As may be seen from electron micrographs and release experiments with radioactively tagged copolymerized gamma globulin as raw material, it consists of polymeric spherules with a diameter of less than 200 nanometers, and preferably less than 80 nanometers, in which the active substance is enclosed and/or adsorbed.

The new process for the production of the microcapsules in the nanometric range which contains biologically or pharmacodynamically active substances or technically useful materials, is characterized according to the invention by the following steps:

1. The boundary surface active auxiliary agents with emulsifying effects which permit the solubilization of water and aqueous solutions or of lipophilic material, where appropriate in suitable solvents, in a hydrophobic or hydrophilic liquid, are dissolved in such a liquid, which is to constitute the hydrophobic or hydrophilic phase.

2. Water and the active material that is to be encapsulated or the aqueous solution of the active material, or the lipophilic active material is added to the solution obtained while stirring, and then the monomers of the polymer to be polymerized are inserted. In this case monomers are used in therapy, which result in a well compatible polymer. As water-soluble monomers one can use more especially acrylamide and N,N'-methylene-bis-acrylamide, or oil-soluble monomers such as, preferably, acrylic acid and acrylic acid methyl ester. In this step of the process one can also proceed in such a way that first water and monomers are stirred alone into the hydrophobic, emulsifier containing liquid, or lipophilic solvent and lipophilic monomers are inserted in the hydrophilic, emulsifier containing liquid, thereupon the concentrated, and where appropriate colloidal, aqueous or oily solution of the active enclosure material is added to the solution obtained.

3. The monomers dissolved in the solubilized, water- or oil-containing micelles, depending on the polymerization technique to be employed, are now polymerized in a manner known per se, whereby the course of polymerization can be monitored by titration of the monomer content.

4. After completion of the polymerization, the polymer obtained, with the encapsulated and adsorbed active material, possibly after removal of the main portion of the liquid of the outside, e.g., continuous phase, is isolated, for example, by distilling off in the vacuum, by ultrafiltration or centrifuging. The product can also be precipitated by the addition of suitable solvents, preferably with aqueous alcohol, or by salting out.

It has been found that relatively short-chained n-alkanes are most suitable as liquid for the hydrophobic phase. They are virtually insoluble in water, optimal for the solubilization of water and do not themselves represent a solvent for the selected monomers and for the biologically active materials, active components such as drugs, or other active substances for enclosure. They are moreover inert, non-poisonous, and easy to remove again from the product obtained.

n-Alkanes which have a boiling point below 0° C. under vacuum are particularly suitable; these are principally n-hexane and n-heptane.

| Boiling Point in ° C. | | | |
|---|---|---|---|
| | 10 mm Hg | 40 mm Hg | 100 mm Hg |
| n-hexane | −25 | − 2.3 | 15.8 |
| n-heptane | − 2.1 | 22.3 | 41.8 |
| water | 11.3 | 34.1 | 51.6 |

It has also been found that the combination of a suitable non-ionogenic emulsifier with an ionogenic emulsifier leads to a substantially better solubilization of the aqueous phase. It is possible with the help of this combination to solubilize a substantially larger volume of water with a smaller total quantity of emulsifier in the organic hydrophobic phase.

As non-ionogenic emulsifiers, good results have been obtained with fatty alcohol polyglycol ethers, e.g., polyethylene lauryl ether with an average of 4 ethylene oxide units in the chain, and as an ionogenic emulsifier, alkaline salts of higher sulphosuccinic acid-bis-alkyl esters, e.g., sulphosuccinic acid-bis-2-ethylhexyl ester sodium salt.

For the capsulation of lipophilic active materials good service has been given by a solubilized mixture in water of Tween 80, e.g., polyoxyethylene sorbitol monooleate, in, for example, ethyl oleate, paraffin, castor oil or other fatty acid esters with acrylic acid derivatives as monomers, preferably acrylic acid or acrylic acid methylester or, where appropriate, some vinyl derivatives.

Polymerization of the monomers is carried out according to known methods, after the addition of catalysts or polymerization initiators, by irradiation, or by a combination of chemical and physical methods such as are described, for example, in U.S. Pat. Nos. 2,875,047, 2,880,152, 2,880,153 and the German Pat. No. 1,081,228.

In selecting the method of polymerization and in particular in adapting the appropriate measures, consideration must be given to the material to be enclosed. This material must not suffer any significant damage during the process employed. To this end certain adaptations of the method are necessary in individual cases.

Thus, it must be taken into consideration that biological material such as antigens consist of sensitive proteins which are destroyed by heat in excess of 55° C., by a pH of less than 2.5, or by the action of oxidizing agents, of which the usual polymerization catalysts consist.

It has furthermore been found that in such cases damage to the proteins can be minimized if the polymerization is performed, depending on requirements, by one of the following methods. One suitable method is the gamma irradiation, e.g., with a $^{60}$Co source, 0.3 Mrad usually being sufficient. In this case, if the material is not sensitive to oxidation, a water-soluble radical generator, as for instance a persulphate, may be used as a polymerization catalyst. In that case, irradiation with visible light, e.g., 300 watt bulb, during about 3 hours and addition of riboflavin (approximately 0.01%) as a sensitizer, and possibly potassium persulphate, leads to polymerization. If ultraviolet light is well tolerated, polymerization can also be performed with ultraviolet light; here solubilized protein even has an accelerating effect on the polymerization time. The duration of ultraviolet irradiation, e.g., with a 70 watt dipping lamp, with a prevailing wavelength of 366 nanometers for about 45 minutes in the presence of protein, otherwise about 3 hours. All of these methods of polymerization call for a nitrogen atmosphere and can be carried out at 30° ± 5° at a pH selected at will.

On the completion of polymerization, the liquid of the hydrophobic phase can be removed by distillation under vacuum, if its presence should prove prejudicial to subsequent processing. The hydrophobic phase used, e.g., n-hexane and water, gives rise to an azeotrope which permits a very gentle distillation at room temperature or, depending on the vacuum even at as low a temperature as 0° C. The micellar capsules with the enclosed active material are then obtained as a rule, in the case of non-sensitive active substances, directly by precipitation with organic solvents, e.g., methanol, which are miscible with water, followed by ultrafiltration or filtration through diaphragm filters and, where requisite, by vacuum drying of the filter residue. As an alternative, the product can also be separated by centrifuging.

In the presence of, for example, labile proteins, precipitation is performed cold with aqueous methanol (40% V/V) and ultrafiltration is carried out by means of a diaphragm filter under excess pressure. Towards the end of filtration, after the emulsifiers, the hydrophobic phase and the greater portion of the methanol solution have been completely removed, the methanol suspension remaining, the filter residue, is diluted with water to a methanol content of some 5% and then lyophilized.

The principal advantages of the method according to the invention reside mainly in the fact that, in contrast to known methods, capsules are obtained which have a particle size 100 to 10,000 times smaller than those heretofore obtained. They have a close distribution of particle diameters and electron microscopically produce the picture of an agglomeration of homogenous, spherical synthetic particles of about equal size. The diameter of the polymeric particles (impregnated with gold for the electron scanning process) is approximately at 800A (80 nanometers), as the scanning photographs show. The lower limit of the particle diameters amounts to 350 – 200A (35 – 20 nanometers), as a test filtration by means of a diaphragm filter: type Sartorius SM 11530, Diaphragm Filter GmbH., 34 Goettingen, mean pore diameter 350–200A as shown. The particles consist of the polymer frame, which encases the active substances mechanically and/or holds them back adsorbitively, whereby a more or less cup-shaped structure of the polymer frame or else filled, but porous particles are obtained, depending on the polarity, the dielectricity constant and the steric conditions of the reaction partners. Because of the extremely small dimensions of the particles, the micellar capsules obtained with the enclosed and adsorbed active material are colloidally soluble in water. This opens up entirely new opportunities for application of therapeutically active substances. More especially, this method allows biologically and pharmacodynamically active material to be administered parentally without hazard, including intravenous injection where appropriate, since a greater or lesser portion of the active substance is enclosed and adsorbed in the structure of the polymerized micelles with a greater or lesser degree of fixity or is partly free, depending on the selection of the quantative ratio between the carrier and the active substance, and can be present in an immediately active form. There is thus a possiblity of carrying out selective long-term therapy by only one single application in which the organism has to tolerate only a minimum of biologically or pharmacodynamically active substance. Moreover, under certain conditions, the substance incorporated in the reticular structure can also come directly into action; this applies in particular to antigens. Thus, an optimal adjuvant action can be achieved, particularly with vaccines. The organism receives over a very long period only an extremely small quantity of antigens and consequently the reticuloendothelial system is constantly stimulated to produce antibodies. The result is a high and stable antibody titre with enduring immunity as the ultimte effect.

Not every active material — protein, drug, pesticide, fertilizer, dye — is equally suitable for incorporation in the micellar reticular structures obtained according to the invention. A particular molecular size and the ability to form at least colloidal, aqueous or oily solutions are essential conditions for incorporation in the micelles occurs during the production only when the active substances are located in the micelles. Substances with a molecular weight up to about 150,000 and which are at least colloid water-soluble or oil-soluble are suitable.

In the case of radioactively tagged human gamma globulin in micelle capsules, kept in vitre for a period of 50 days at 37° C in an agitated phosphate buffer solution only 20% of the gamma globulins were liberated unaltered from the time measurement was commenced, which shows that the largest part of the active substance had been well encapsulated.

On the other hand results with gamma globulin in an immunization test with guinea pigs in viva show that high and relatively persistent antibody titres are obtained very soon.

The following tables show the results of comparative experiments with traditional aluminum oxide adjuvant (Table I) and Freund's complete adjuvant (Table II) shows the use of human gamma globulin. Table III shows antitoxin titres such as are obtained after the immunization of guinea pigs with various tetanus toxoid preparations.

Table I

| Group | Preparation | Dosage (relates to IgG) | Vacc. Schedule (Vacc. days) 0 14 22 72 | Mean Titre (Haemagglutination Misrotechnique) Number of Animals / Standard Deviation | | | | | Commentary |
|---|---|---|---|---|---|---|---|---|---|
| | | | | 1st bleeding | 2nd bleeding | 3rd bleeding | 4th bleeding | 5th bleeding | |
| 1 | IgG starting material | 0.3mg/kg | + + + + | I : 4 9 / | I : 2.2 8 / | I : 6.4 8 / 40 | I : 1.2 8 / 61 | I : 6.1 8 / 736 | Booster I-3 like primary vacc. |
| 2 | IgG starting material | 0.3mg/kg | + + | I : 16 10 / | I : 2 10 / | I : 9.1 10 / 1.6 | I : 1.4 7 / 1.2 | I : 4.4 7 / 56 | |
| 3 | IgG starting material + Al-oxide (4mg/ml) | 0.3mg/kg | + + | I : 16 3 / | I : 32 8 / | I : 3.6 7 / 46 | I : 2.1 6 / 11 | I : 113 6 / 5.6 | |
| 4 | IgG copolymerized | 0.3mg/kg | + + | I : 8 4 / | I : 3.5 4 / | I : 3.4 3 / 1.5 | I : 3.4 3 / 1.5 | I : 170 3 / 1.7 | |
| 5 | IgG copolymerized | 0.3mg/Kg | + + + | I : 16 4 / | I : 3.3 4 / | I : 81 3 / 8.4 | I : 8 1 / | I : 512 1 / | 1. Booster like primary vacc. |
| 6 | IgG copolymerized | 0.3mg/kg | + + + | I : 64 5 / | I : 2.4 5 / | I : 88 5 / 13 | I : 8.2 5 / 7.6 | I : 256 2 / 0 | 1. Booster with IgG start. material |
| 7 | IgG copolymerized | 1 mg/kg | + + | I : 256 5 / | I : 95 5 / | I : 37 5 / 25 | I : 26 5 / 6.3 | I : 1740 4 / 6.0 | |
| 8 | IgC copolymerized | 1 mg/kg | + + + | I : 64 5 / | I : 64 5 / | I : 320 5 / 1.3 | I : 16 4 / 1.4 | I : 85 4 / 23 | 1. Booster like primary vacc. |
| 9 | IgG copolymerized | 1 mg/kg | + + + | I : 128 5 / | I : 51 4 / | I : 287 4 / 13 | I : 27 3 / 1.5 | I : 512 1 / | 1. Booster 0.3mg/kg start. material |
| 10 | IgG copolymerized IgG starting material | 1 mg/kg 0.3mg/kg | + + | I : 256 9 / | I : 51 8 / | I : 23 8 / 1.4 | I : 16 6 / 1.1 | I : 324 7 / 8.8 | |

Immunization of guinea pigs (subcutaneous) with IgG preparations
Bloodings on 14th, 21st, 35th, 56th and 83rd day, ensuing booster injection = 1, booster injection on 72nd day with 1 mg/kg IgG starting material.

TABLE 2

| Group | Preparation | Dosage (relates to IgG | Vacc. Schedule (Vacc. days) 0 21 | mean titre (haemagglutination misrotechnique) Number of animals / Standard deviation | | | | Commentary |
|---|---|---|---|---|---|---|---|---|
| | | | | 1st bleeding | 2nd bleeding | 3rd bleeding | 4th bleeding | |
| 11 | IgG starting material | 1 mg/kg | + + | I : 2.5 15 / 9.0 | I : 6.5 14 / 6.4 | I : 31 13 / 5.8 | I : 7 9 / 4.4 | Booster 1 mg/kg start. mat. |
| 12 | IgG Starting material + compl. Freund adj. 1:1 | 1 mg/kg | + + | I : 51 20 / 60 | I : 272 17 / 5.5 | I : 1954 14 / 4.8 | I : 930 10 / 4.6 | Booster 1 mg/kg start. mat. |
| 13 | Micelle polymers (116 mg) IgG starting material | 1 mg/kg | + + | I : 3 15 / 3.6 | I : 3.7 13 / 6.0 | I : 33 12 / 2.0 | I : 2 11 / 13 | Booster 1 mg/kg start. mat. |

Immunization of guinea pigs (intramuscular) with IgG preparations
Bloodings on 10th, 20th, 30th and 60th day, ensuing booster injection = 1.

TABLE 3

| Group | Preparation | Dosage (toxoid) | Antitoxin - titre IU/ml (determination of L+ dose on mice) (Number of animals in pool) | | | |
|---|---|---|---|---|---|---|
| | | | 1st bleeding | 2nd bleeding | 3rd bleeding | 4th bleeding |
| 14 | Tetanus toxoid copolymerized | 5 Lf | >0.01<0.05 (5) >0.05<0.1 (4) >0.05<0.1 (5) >0.01<0.05 (5) | >2.0<5.0 (5) >5.0<10.0 (5) >1.0<5.0 (4) | approx. 2.0 (5) >2.0<5.0 (4) >2.0<5.0 (4) | >1.0<2.0 (10) |
| 15 | Tetanus toxoid copolymerized | 50 Lf | >2.0<5.0 (4) >2.0<5.0 (5) >5.0<10.0 (4) | approx. 10.0 (5) >10.0<20.0 (4) | >5.0<10.0 (6) | >2.0<5.0 (9) |
| 16 | Tetanus toxoid copolymerized + starting toxoid | 5 Lf 5 Lf | >2.0<5.0 (4) >0.05<0.1 (4) >0.01<0.05 (5) | >5.0<10.0 (4) >2.0<5.0 (5) | >5.0<10.0 (5) >2.0<5.0 (5) | approx. 2.0 (4) |
| 17 | Tetanus toxoid copolymerized + starting toxoid | 50 Lf 50 Lf | >0.5<1.0 (5) 1.0 (5) >1.0<2.0 (5) | >2.0<5.0 (4) >5.0<10.0 (4) | >5.0<10.0 (5) >5.0<10.0 (5) | 5.0 (5) |
| 18 | Tetanus toxoid + Al-phosphate | 5 Lf | >0.5<1.0 (5) >1.0<2.0 (5) | >5.0<10.0 (5) >approx. 5.0 (5) >5.0<10.0 (5) | >5.0<10.0 (5) >2.0<5.0 (5) | >2.0<5.0 (7) |
| 19 | Tetanus toxoid | | approx. 1.0 (4) >1.0<2.0 (5) | | | |

TABLE 3-continued

| Group | Preparation | Dosage (toxoid) | 1st bleeding | Antitoxin - titre IU/ml (determination of L+ dose on mice) (Number of animals in pool) | | |
|---|---|---|---|---|---|---|
| | | | | 2nd bleeding | 3rd bleeding | 4th bleeding |
| | + Al-phosphate | 50 Lf | 1.0 (5) >2.0<5.0 (5) | >2.0<5.0 (5) approx. 10.0 (6) | >5.0<10.0 (5) 11.0 (5) | >5.0<10.0 (8) |

Immunization of guinea pigs (intramuscular) with tetanus toxoid preparation
Bleedings after 3, 6, 12 and 20 weeks, no booster injection.

The invention is explained in more detail below by reference to practical examples; these may be divided into three working processes: (a) solubilization, (b) polymerization, and (c) isolation and purification.

EXAMPLE I 12.0 grams sulphosuccinic acid-bis-2-ethylhexyl ester as sodium salt (Aerosol OT), and 6.0 grams polyoxyethylene (4) -laurylether with an average of 4 ethylene oxide units in the chain (tenside LA-55-4, Hefti AG, Zurich) are dissolved in 20.0 grams n-hexane; the solution is filtered until sterile. While stirring, from this point onwards under sterile conditions, 10.0 grams aqueous toxoid solution (diptheria or tetanus toxoid with 100 Lf/ml) is added, care being taken to add the toxoid slowly, in order that the solution remains clear. After a further 20.0 grams n-hexane have been added, the monomers are stirred in, viz., 0.250 grams N, N'-methylene-bis-acrylamide and 2.000 grams acrylamide. Once the crystalline components have been completely dissolved, the total weight is brought up to 110.0 grams with n-hexane.

The solution is covered with a layer of nitrogen, sealed tight, and exposed continuously to the radiation of a cobalt 60 source at about 20°–30° C. A dose of 0.3 Mrad is sufficient to ensure polymerization. The end of polymerization, i.e., the disappearance of the monomers, can be checked with an acidimetric color titration method to determine alpha, beta-unsaturated compounds by means of a reaction with morpholine (F. E. Critchfield, G. L. Funk, J. B. Johnson; Analyt. Chem. 28, 78–79, 1956).

After polymerization is complete the n-hexane hydrophobic phase is removed by gentle distillation at room temperature under a vacuum created by a waterjet pump. From the remaining concentrated aqueous solution of product and tenside, the tensides are removed by ultrafiltration with distilled water (diaphragm: Amicon PK 30) under an excess pressure of nitrogen (approximately 2–4 atmospheres). A colloidal aqueous solution of the product of microcapsules having a diameter in the range of 20 to 200 nanometers is obtained and can be lyophilized (freeze-dried). The mean diameter of the microcapsules is less than about 50 nanometers.

EXAMPLE II 12.0 grams Aerosol OT and 6.0 grams LA-55-4 are dissolved in 80.0 grams n-hexane until the solution is clear, 5.0 grams distilled water is solubilized therein drop by drop, and the crystalline monomers 0.250 grams N,N'-methlene-bis-acrylamide and 2,000 grams acrylamide are dissolved. The solution is filtered until sterile. Under sterile conditions, 5.0 grams tetanus toxoid solution with 3,100 Lf/ml is added drop by drop.

The polymerization was carried out as described in Example I, by gamma irradiation.

After polymerization is complete, the polymeric product containing antigen, can be gently completed (precipitated) at 5° C with 40% aqueous methanol. Centrifuging or ultrafiltration at 5° C follows in order to remove tensides. Freeze-drying (lyophilization) (methanol content preferably adjusted to below 5% with water) or ultrafiltration with water removes other solvents and yields the desired product of microcapsules having a diameter in the range of 20 to 200 nanometers.

EXAMPLE III 45.0 grams Aerosol OT and 25.0 grams LA-55-4 are dissolved in 215.0 grams n-hexane. 2.5 grams ethanol, 2.5 grams methanol, 40.0 grams of distilled water, 1.000 grams N, N'-methylene-bis-acrylamide and 8.000 grams acrylamide are then added in that order and dissolved until the solution is clear. The solubilized mixture is filtered until sterile, and the weight made up to 340.0 grams with n-hexane. While stirring, and under sterile conditions from this point onwards, 10.0 grams of a gamma globulin solution (aggregate-free in tris-NCl + NaCl 0.100 grams; approximately 1.4% human IgG) are solubilized drop by drop.

The polymerization was carried out by gamma irradiation, as described in Example I.

The isolation of the micelle capsules having diameters in the range of 20–200 nanometers can take place, corresponding to Examples I or II.

EXAMPLE IV 12.0 grams Aerosol OT and 6.0 grams LA-55-4 are dissolved in 80.0 grams n-hexane; 35.0 grams distilled water is slowly solubilized, while the solution is being stirred, and the crystalline monomers 0.500 grams N, N'-methylene-bis-acrylamide and 4.000 grams acrylamide are dissolved therein. The solution is filtered until sterile and 0.300 grams urease (freeze dried product, water-soluble, "Merck") is introduced to form a micellar solution.

The solution obtained is irradiated from the inside by an ultraviolet dipping lamp (quartz burner 70 Watts) for 45 minutes in the cylindrical reaction vessel, while stirring and at a temperature constancy of 35±5° C and with a nitrogen stream continuously bubbling through the solution, until the monomers disappear.

After polymerization is complete the solution is mixed in excess with methanol containing not less than 80% alcohol. The product of microcapsules having a diameter in the range of 20–200 nanometers is precipitated and can be extracted by centrifuging or filtered under pressure and washed.

EXAMPLE V 50 grams water was added, while stirring, to a solution of 5.0 grams toluene, 50 milligrams diethyl-p-nitrophenyl-monothiophosphate and 10 grams polyoxyethylene-sorbitan-monooleate (Tween 80), 1.5 grams acrylic acid methyl ester was stirred into this solution.

In this solution, placed in a cylindrical, double-walled, thermostatistable reaction vessel of pyrex glass (internal diameter of 6 centimeters) 0.2 milligrams riboflavin 5'-sodium phosphate and 0.2 milligrams $K_2S_2O_8$ are dissolved, while stirring. While stirring constantly and at a constant temperature of 35°± 5° C the solution is continuously perfused with a stream of nitrogen bubbles, and irradiated from outside half way up the column of liquid at a distance of 15 centimeters with a light bulb, type Osram (300 Watts) for seven hours, until the monomers disappear.

The isolation of the micelle capsules having diameters in the range of 20–200 nanometers with the insecticide was accomplished according to Example IV.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. Microcapsules of encapsulated active material, said microcapsules being colloidally soluble in water, said capsules comprising a gel of polymerized acrylamide, polymerized N,N'-methylene-bis acrylamide, polymerized acrylic acid, or methyl acrylate, said microcapsules having a diameter in a micellar order of magnitude of 20–200 nanometers.

2. The microcapsules as in claim 1, characterized in that the mean diameter of the capsules is below 80 nanometers and the polymeric material is polymerized N, N'-methylene-bis-acrylamide.

3. A process for the production of microcapsules of polymeric material having encapsulated active materials, said microcapsules being colloidally soluble in water and having a diameter in a micellar order of magnitude of 20–200 nanometers, said process comprising:
   a. dissolving boundary surface-active auxiliary emulsifying substances in a hydrophobic liquid to form micellar reaction spaces in said hydrophobic liquids;
   b. adding to said hydrophobic liquid while stirring, an aqueous solution of an active material to be encapsulated and an encapsulating monomer from the group consisting of acrylamide, N,N'-methylene-bis-acrylamide, acrylic acid, and methyl acrylate, said aqueous solution substantially assuming a presence in said micellar spaces;
   c. polymerizing the micellarly dissolved monomers to form microcapsules having said active material absorbed and/or encapsulated in said microcapsules, said polymerization taking place in said micellar spaces in said hydrophobic liquid to produce microcapsules having a diameter of a micellar order of magnitude of 20–200 nanometers; and
   d. isolating the resulting microcapsules from the hydrophobic liquid.

4. The process of claim 3 wherein the monomer is first dissolved in water and a solution of the active substance is added to said monomer solution prior to mixing with the hydrophobic liquid.

5. The process of claim 3, in which n-lower alkane, having a boiling point below 0° C under vacuum is used as hydrophobic liquid.

6. The process of claim 5 in which the n-lower alkane is n-hexane or n-heptane.

7. The process of claim 3, in which paraffin, ethyl oleate, castor oil or other vegetable oils are used as the hydrophobic liquid.

* * * * *